United States Patent
Wenz et al.

(10) Patent No.: US 7,250,260 B2
(45) Date of Patent: Jul. 31, 2007

(54) MULTI-STEP BIOASSAYS ON MODULAR MICROFLUIDIC APPLICATION PLATFORMS

(75) Inventors: H. Michael Wenz, Redwood City, CA (US); Alexander Jung, Sipplingen (DE); Simone Guenther, Ueberlingen (DE); Michael Steinwand, Owingen (DE); Timothy G. Geiser, San Mateo, CA (US)

(73) Assignee: Applera Corporation, Foster City, CA (US)

( * ) Notice: Subject to any disclaimer, the term of this patent is extended or adjusted under 35 U.S.C. 154(b) by 50 days.

(21) Appl. No.: 11/059,824

(22) Filed: Feb. 16, 2005

(65) Prior Publication Data

US 2006/0035243 A1 Feb. 16, 2006

Related U.S. Application Data (60) Provisional application No. 60/545,674, filed on Feb. 18, 2004.

(51) Int. Cl.
*C12Q 1/68* (2006.01)
*C12P 19/34* (2006.01)

(52) U.S. Cl. .................. 435/6; 435/91.1; 435/91.2
(58) Field of Classification Search .................. None
See application file for complete search history.

(56) References Cited

U.S. PATENT DOCUMENTS

| 5,830,711 | A | | 11/1998 | Barany et al. |
|---|---|---|---|---|
| 5,863,708 | A | * | 1/1999 | Zanzucchi et al. .......... 430/320 |
| 5,872,010 | A | | 2/1999 | Karger et al. |
| 6,027,889 | A | | 2/2000 | Barany et al. |
| 6,140,110 | A | | 10/2000 | Vinayagamoorthy et al. |
| 6,461,812 | B2 | | 10/2002 | Barth et al. |
| 6,485,690 | B1 | | 11/2002 | Pfost et al. |
| 2002/0006359 | A1 | | 1/2002 | Mathies et al. |
| 2002/0117517 | A1 | | 8/2002 | Unger et al. |
| 2004/0074557 | A1 | | 4/2004 | Zengerle et al. |

FOREIGN PATENT DOCUMENTS

| DE | 199 17 029 A1 | 11/2000 |
|---|---|---|
| WO | WO 00/56443 A1 | 9/2000 |
| WO | WO 01/21310 A2 | 3/2001 |
| WO | WO 01/24932 A1 | 4/2001 |
| WO | WO 02/15949 A2 | 2/2002 |
| WO | WO 02/16021 A1 | 2/2002 |
| WO | WO 02/057015 A2 | 7/2002 |
| WO | WO 02/057015 A3 | 7/2002 |

OTHER PUBLICATIONS

International Search Report for International Application No. PCT/US2005/004991 dated Aug. 1, 2005.
PCT Written Opinion of the International Searching Authority.

* cited by examiner

*Primary Examiner*—Young J. Kim (57) ABSTRACT

Apparatus and method for performing sequential bioassays with microfluidic transfers.

21 Claims, 11 Drawing Sheets

MULTI-STEP BIOASSAYS ON MODULAR MICROFLUIDIC APPLICATION PLATFORMS

CROSS-REFERENCE TO RELATED APPLICATIONS

This application claims a priority benefit under 35 U.S.C. § 119(e) from U.S. Provisional Application Ser. No. 60/545,674 filed Feb. 18, 2004, which is incorporated herein by reference.

FIELD

The present teachings relate to systems and methods for detection of a target polynucleotide in a sample.

INTRODUCTION

In the biological field, bioassays of samples can provide analysis of complex genetic systems. These bioassays include oligonucleotide ligation assay (OLA), polymerase chain reaction (PCR), and other reactions such as ligase chain reaction, antibody binding reaction, and hybridization assay. These and other bioassays can be performed as sequential batch operations on a single sample. As such, the reactions can include handling the sample with the target polynucleotide while transferring between reactions. The term "sample" as used herein can refer to biological fluids that contain the target polynucleotide. Bioassays can be complex procedures including deposition, dissolving, pipetting, liquid transfer, washing, cleaning, incubating, reacting, and other handling steps. Performing sequential bioassays in a high throughput mode (e.g. multiple parameters tested in parallel) and in a high density (e.g. small volumes in a small area) can often be limited by these complex handling steps. Microfluidics can provide the technology to perform such bioassays in a high throughput mode and in a high density. Microfluidics to miniaturize the scale of these bioassays can result in an increase in complex handling steps for sequentially performed bioassays. It can be desirable to select bioassays to be performed in sequence so as to reduce the complex handling steps. Open systems that require an intermediate transfer step by manual or robotic transfer from one reaction vessel to another can be limited in miniaturization by the minimum volume that can be manually or robotically transferred. It can be desirable to provide a closed system with microfluidic transfer between platforms to avoid manual or robotic transfer limitations.

SUMMARY

A system for detecting a target polynucleotide in a sample the system including an OLA platform comprising a plurality of OLA wells, and a PCR platform comprising a plurality of PCR wells, wherein the OLA wells are in fluid communications with the PCR wells, wherein the system is a closed system capable of transferring a plurality of OLA products from the OLA wells to the PCR wells.

It is to be understood that both the foregoing general description and the following description of various embodiments are exemplary and explanatory only and are not restrictive.

BRIEF DESCRIPTION OF THE DRAWINGS

The accompanying drawings, which are incorporated in and constitute a part of this specification, illustrate various embodiments. In the drawings.

DESCRIPTION OF VARIOUS EMBODIMENTS

Reference will now be made to various exemplary embodiments, examples of which are illustrated in the accompanying drawings. Wherever possible, the same reference numbers are used in the drawings and the description to refer to the same or like parts.

The term "target polynucleotide" as used herein refers to both multiple separate polynucleotide strands and multiple regions on the same polynucleotide strand that are separately amplified and/or detected. A target polynucleotide can be a single molecule of double-stranded or single-stranded polynucleotide, such as a length of genomic DNA (gDNA), cDNA or viral genome including RNA, or a mixture of polynucleotide fragments, such as gDNA fragments or a mixture of viral and somatic polynucleotide fragments from an infected sample. A target polynucleotide can be double-stranded DNA which is denatured, e.g., by heating, to form single-stranded target molecules capable of hybridizing with primers and/or oligonucleotide probes.

The term "polynucleotide" as used herein means a linear oligomer of nucleosides or analogs thereof, including deoxyribonucleosides, ribonucleosides, and the like, from a few tens of units in length to many thousands of units in length.

The term "oligonucleotide" as used herein refers to linear oligomers of natural or modified monomers or linkages, including deoxyribonucleosides, ribonucleosides, polyamide nucleic acids, and the like, capable of specifically binding to a target polynucleotide by way of a regular pattern of monomer-to-monomer interactions, such as Watson-Crick type of base pairing, and capable of being ligated to another oligonucleotide in a template-driven reaction.

The term "thermal cycling" as used herein refers to maintaining at an increased temperature and/or maintaining at a decreased temperature a bioassay reaction volume for certain time intervals and at certain rates of heating and/or cooling as known in the art of bioassays.

According to various embodiments, selection of bioassays that can be performed in sequence so as to reduce handling steps depends on the robustness of the bioassays and their order in the sequence so that the second bioassay can receive the product of first bioassay without any intermediate steps. According to various embodiments, selection of the bioassays that can be performed in sequence so as to reduce the handling steps depends on the robustness of the bioassays to be able to operate in small volumes with a minimal transfer of product from the first bioassay to the second bioassay. According to various embodiments, selection of the bioassays that can be performed in sequence so as to reduce the handling steps depends on the robustness of the bioassays to be able to sustain reaction conditions other than their intended reaction conditions such that the second bioassay does not substantially commence until the first bioassay is complete and/or the first bioassay does not substantially continue in the second bioassay.

According to various embodiments, a first bioassay and a second bioassay can be conducted in sequence in an open system. The first bioassay can include dispensing a sample with first reagent into a first reaction vessel, reacting the sample, robotically transferring a fraction of the first bioassay product to the second bioassay with second reagent into a second reaction vessel, and reacting to form second product. The first and second reagent can be different or they can be the same.

Figure 1:
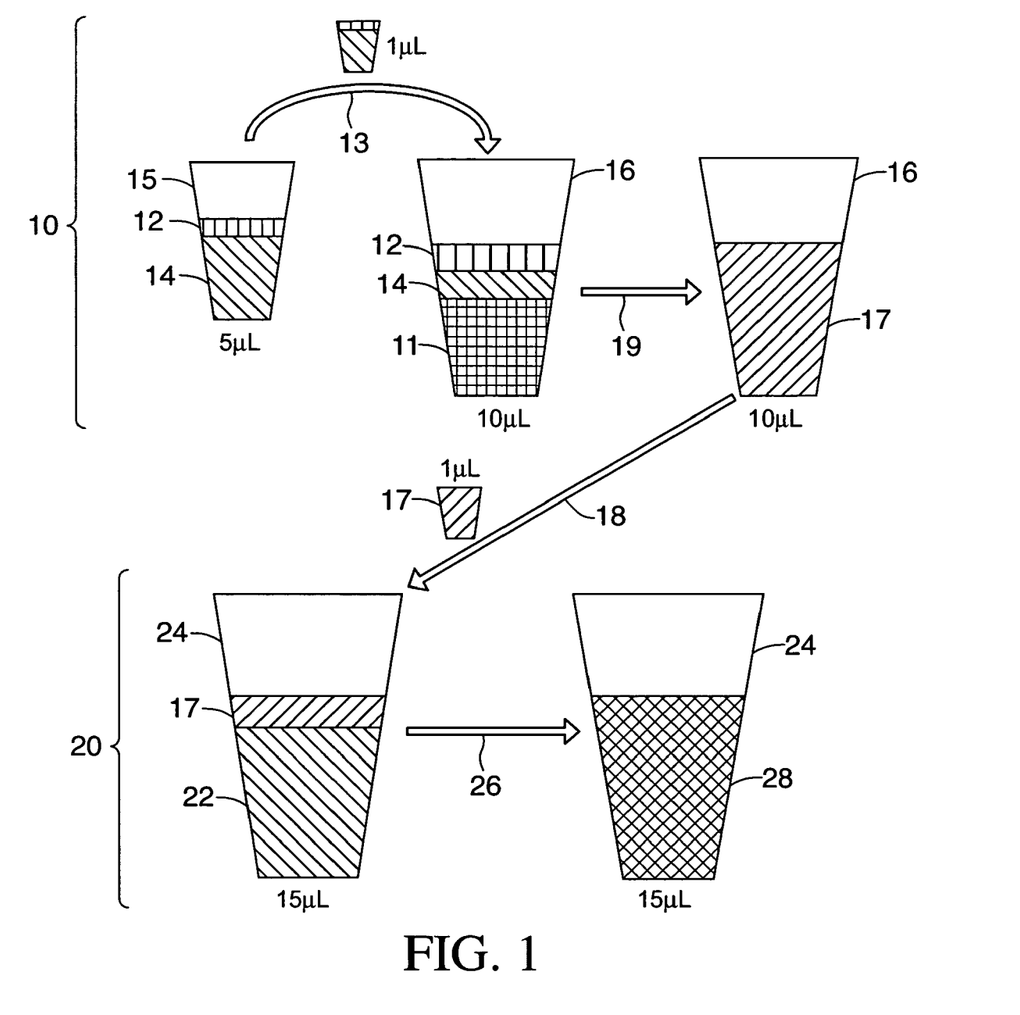
FIG. 1 illustrates various embodiments of an open system with sequential batch bioassays.

According to various embodiments, the first bioassay can be OLA and the second bioassay can be PCR. OLA and PCR can be selected because these bioassays can meet the robustness criteria as described herein as exemplified by U.S. Pat. Nos. 6,027,889 and 5,830,711. In an open system as illustrated in FIG. 1, OLA and PCR include dispensing a preformulated ligation buffer 14 to dilute the sample 12 in dilution vessel 15. The smallest volumes that can be transferred by robotic transfer 13 are 1.0 microliter. A 5.0 microliter OLA dilution volume (1.0 microliters sample 12 and 4.0 microliters buffer 14) can supply the robot with 1.0 microliter to transfer into an OLA probe mixture 11 providing an OLA reaction volume of 10.0 microliters in OLA reaction vessel 16. The OLA reaction volume can be thermally cycled 19 to produce an OLA product 17. The robot can transfer 1.0 microliter of OLA product 17 to the PCR reagent 22 in PCR reaction vessel 24, via robotic transfer 18 providing a PCR reaction volume of 15.0 microliters. The PCR reaction volume can be thermally cycled 26 to produce a PCR product 28. The open system limits the amount transferred to 1.0 microliter. The remainder of the OLA reaction volume is wasted while only 50-2000 nanoliters are used for subsequent PCR.

According to various embodiments, a first bioassay and a second bioassay can be conducted in sequence in a closed system. The first bioassay and the second bioassay can be carried out in the same volume with a microfluidic transfer.

Figure 2:
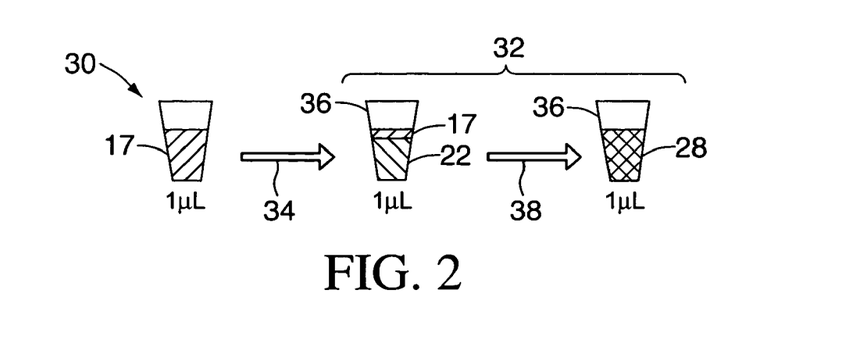
FIG. 2 illustrates various embodiments of a closed system with sequential batch bioassays.

According to various embodiments, the first bioassay can be OLA and the second bioassay can be PCR. OLA and PCR can be selected because these bioassays can meet the robustness criteria as described herein as exemplified by U.S. Pat. Nos. 6,027,889 and 5,830,711. In a closed system, as illustrated in FIG. 2, the OLA bioassay 30 includes an OLA reaction volume that can be 1.0 microliters and the PCR bioassay 32 includes a PCR reaction volume that can be 1.0 microliters with a 50-100 nanoliter microfluidic transfer 34 of OLA product 17. The OLA product 17 can be transferred to PCR reaction vessel 36 and with PCR reagent and thermally cycled 38 to produce PCR product 28. According to various embodiments, 70 nanoliters of OLA product can be transferred to the PCR bioassay.

According to various embodiments, the first bioassay platform can include an input for receiving the sample, channels for distributing the sample to a plurality of first bioassay wells. The first bioassay wells can include a first bioassay reagent, where the first bioassay reagent can be pre-positioned and/or dried in the first bioassay wells for storage.

Figure 3:
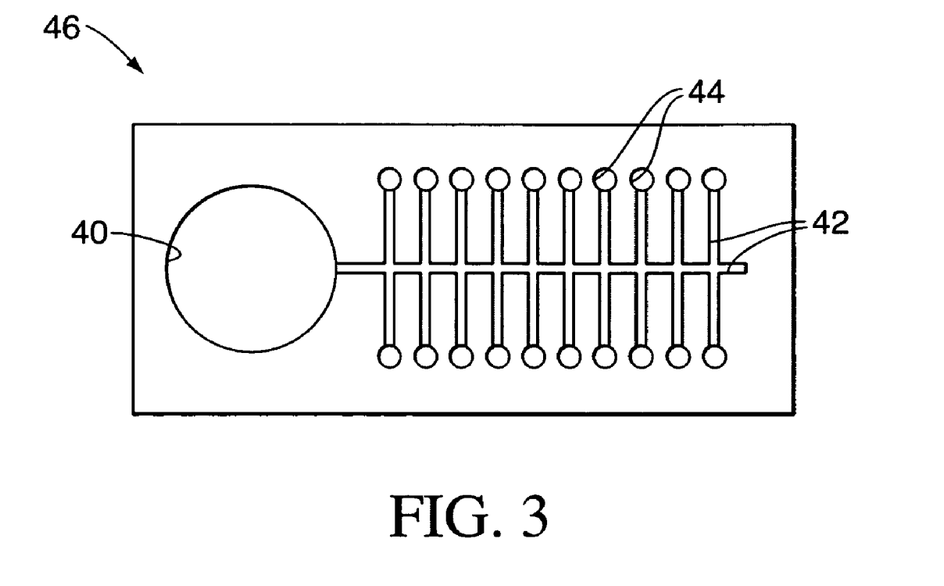
FIG. 3 illustrates a perspective view of various embodiments of a bioassay platform.

According to various embodiments, the first bioassay can be OLA. As illustrated in FIG. 3, the OLA platform 46 can be configured in a planar orientation. The OLA platform 54 can be incorporated into an OLA card. The OLA platform can include an input 40 for receiving the sample, channels 42 for distributing the sample to a plurality of OLA wells 44, and/or a microfluidic system (not shown) for transferring the OLA product to the subsequent bioassay. The OLA wells 44 can include OLA probes and can be configured for OLA thermal cycling.

According to various embodiments, the second bioassay platform can include channels connecting the plurality of first bioassay wells to a plurality of second bioassay wells. The channels can be positioned so that a channel connects each first bioassay well to a corresponding second bioassay well. The second bioassay wells can include a second bioassay reagent, where the second bioassay reagent can be pre-positioned and/or dried in the second bioassay wells for storage.

Figure 4:
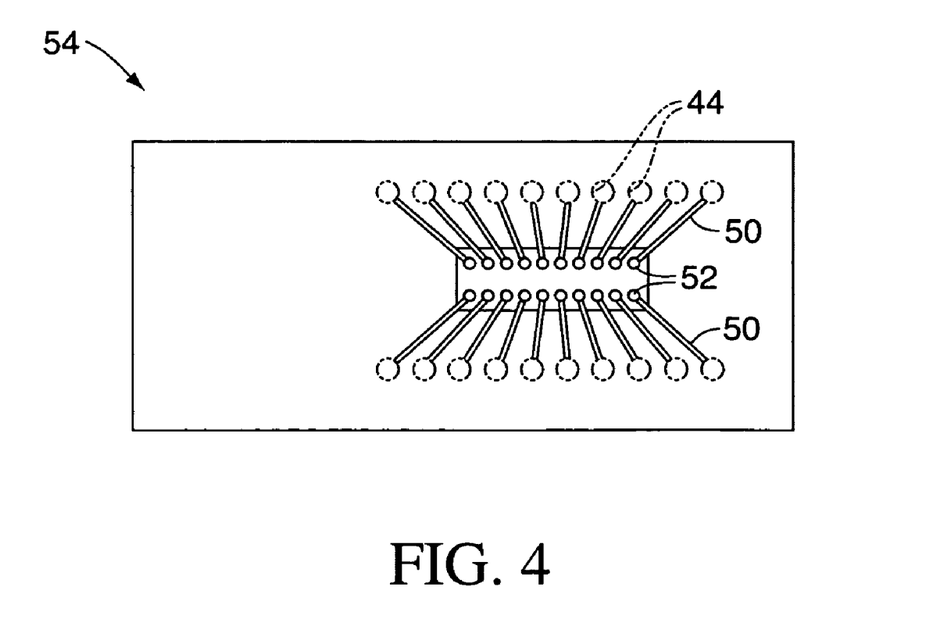
FIG. 4 illustrates a perspective view of various embodiments of a bioassay platform.

According to various embodiments, the second bioassay can be PCR. As illustrated in FIG. 4, PCR platform 54 can be configured in a planar orientation. The PCR platform 54 can be incorporated into a PCR card. The PCR platform 54 can include channels 50 for receiving the first bioassay product and PCR wells 52. The PCR wells 52 can include PCR reagents and can be configured for PCR thermal cycling. According to various embodiments, the first bioassay can be OLA. The channels 50 on the PCR platform 54 can be positioned to receive the plurality of OLA products from each OLA well 44 (shown in ghost outline).

Figure 5A:
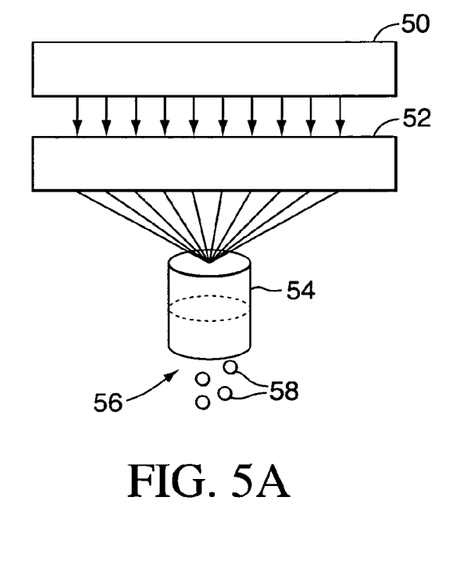
FIG. 5 illustrates a cross-sectional view of various embodiments of a multiple bioassay platforms in sequence.
Figure 5B:
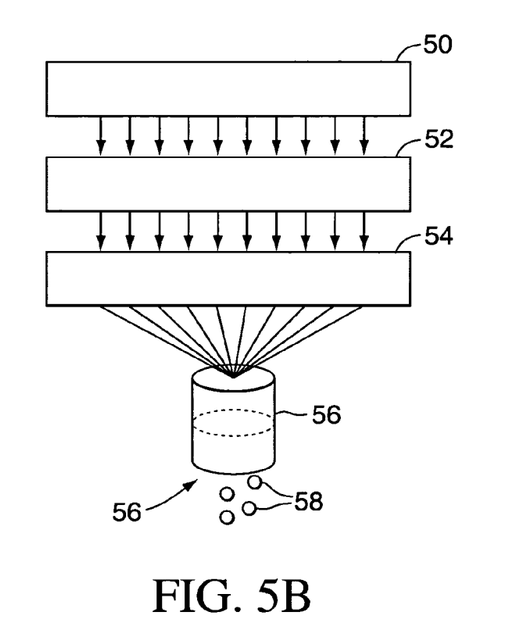

According to various embodiments, the first bioassay platform and the second bioassay platform can be positioned on separate cards which can be mated to allow sequential batch bioassays. According to various embodiments, the mated bioassay cards can be mated with a purification card to treat the second assay product prior to detection. According to various embodiments, the second bioassay products can be channeled to an outlet for detection. FIG. 5A illustrates a first bioassay card 50 mated with a second bioassay card 52 which channels into a purification tip 54 and outlet 56 where the second bioassay product 58 can be collected for detection. FIG. 5B illustrates a first bioassay card 50 mated with a second bioassay card 52 mated with a purification card 60 which channels into tip 62 and outlet 56 where the second bioassay product 58 can be collected for detection. The vertical arrows in FIGS. 5A and 5B indicate pluralities of products transferred from each card. According to various embodiments, first bioassay card 50 can be an OLA card, second bioassay card 52 can be a PCR card, purification tip 54 can include beads, and purification card 60 can be chip card with capillary electrophoresis polymers. According to various embodiments, the purification beads can include ion-exchange beads or streptavidin coated magnetic beads.

Figure 6:
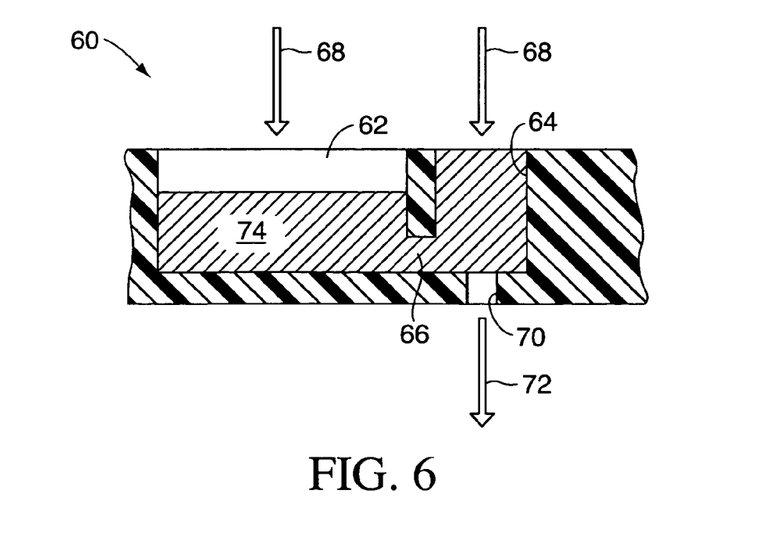
FIG. 6 illustrates a cross-sectional view of various embodiments of a microfluidic system for transferring liquid between bioassay platforms.

According to various embodiments, FIG. 6 illustrates a microfluidic system for transferring liquid between bioassay platforms. Such microfluidic systems are known in the art and are manufactured by IMTEK (University of Freiburg, Germany). FIG. 6 illustrates a transferring system 60 with a well 62 for holding the first bioassay product 74, a nozzle 64, linked via a connecting channel 66. Pressure pulse 68 provides a substantially equal force to well 62 and nozzle 64. Flow resistance in the connecting channel 66 and nozzle 64 can be designed such that the volume flowing in the connecting channel 66 is small compared to the volume flowing through nozzle 64 that regulates the microfluidic transfer 72 through opening 70. The transferring system 60 can be positioned in the first bioassay platform as illustrated in FIG. 6 or between the first bioassay platform and the second bioassay platform.

According to various embodiments, microfluidic systems for transferring liquid between bioassay platforms can include three-dimensional structures constructed of multiple layers of elastomeric material with control channels to provide pressure to the nozzle to dispense the liquid (Fluidigm, Corp., San Francisco). The activation can be pneumatic, electrostatic, piezoelectric, thermal or magnetic. According to various embodiments, microfluidic systems for transferring liquid between bioassay platforms can include microfluidic ball valves (Micronics, Inc., Redmond).

According to various embodiments, the first bioassay can be a digest of gDNA or thermal shearing of gDNA. The second bioassay can be any of the bioassays described herein such as OLA and/or PCR. Several bioassays require a bioassay to prepare the gDNA to be transferred to the subsequent bioassay. Bioassays to prepare gDNA can require hands-on manipulation or pipetting robots. Bioassays to prepare gDNA can provide the robustness as described herein. A small transfer of prepared gDNA on the order of 50.0 nanoliters can provide a first assay product for subsequent bioassays. It can be desirable to replace these open system transfers with a closed system microfluidic transfer as described herein. According to various embodiments, a bioassay to prepare gDNA can be configured into a bioassay card and mated to an OLA card which is mated to a PCR card.

According to various embodiments, the bioassays can be proteomics bioassays and/or affinity assays where it is desirable to have a microfluidic transfer as described herein.

EXAMPLES

The present teachings of sequential OLA and PCR through microfluidic transfer were applied to single nucleotide polymorphism (SNP) identification using SNPlex™ (Applied Biosystems, Foster City) to perform genotyping studies in multiplex reactions of 48 per well in 4 wells. More wells can be positioned such as 24, 48, 96, 384 or greater per platform. To prepare the 48-plex probes, a kinase step was integrated into the assay to ensure the quantitative phorsphorylation of the probes and their capability to be ligated. Following the allele-specific assay step, an oligonucleotide ligation was performed. Only the allele-specific oligonucleotide (ASO) in the genomic DNA was ligated to the locus-specific oligonucleotide (LSO). The OLA reaction included 5 hours of thermal cycling with slow temperature ramps. The OLA probes contained double-stranded protection groups, which were removed by exonuclease digest after the ligation. The purified OLA products were then amplified in a universal PCR reaction (one primer pair for all 48 contained tests). The reverse primer was biotinylated for later purification. PCR purification was completed with streptavidin-coated MTPs. The double strands were denatured and excess DNA was washed off. Prior to detection, ZipChute™ were hybridized to the denatured double strands to recognize the SNP locus specifically and modify the mobility of denatured strand in capillary electrophoresis. In various embodiments, chart 1 illustrates the steps that can be integrated on different platforms and liquid transfers between those platforms. Chart 1 illustrates two examples of platforms and liquid transfer between those platforms with (A) representing a two-platform system and (B) representing a multiple platform system.

CHART 1

| SNP Assay Steps | Location of Step (A) | Location of Step (B) |
| --- | --- | --- |
| gDNA preparation | OLA platform | Prep platform |
| Phosphorylation of probes | OLA platform | Prep platform |
| OLA reaction | OLA platform | OLA platform |
| OLA purification | OLA platform | Purification platform |
| PCR reaction | PCR platform | PCR platform |
| PCR purification | PCR platform | Purification platform |

Figure 7:
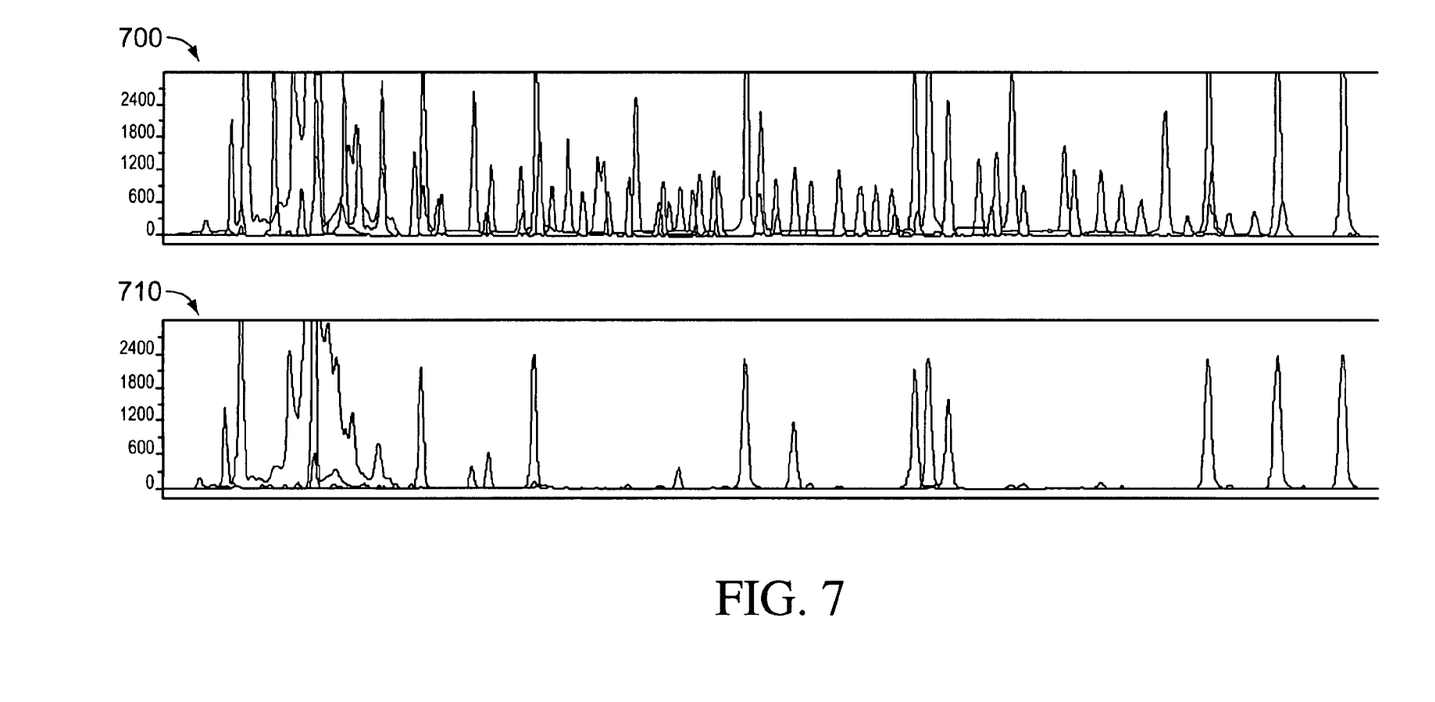
FIGS. 7-14 illustrate graphs of results from platform implementation according to the present teachings of a single nucleotide polymorphism assay.
Figure 8:
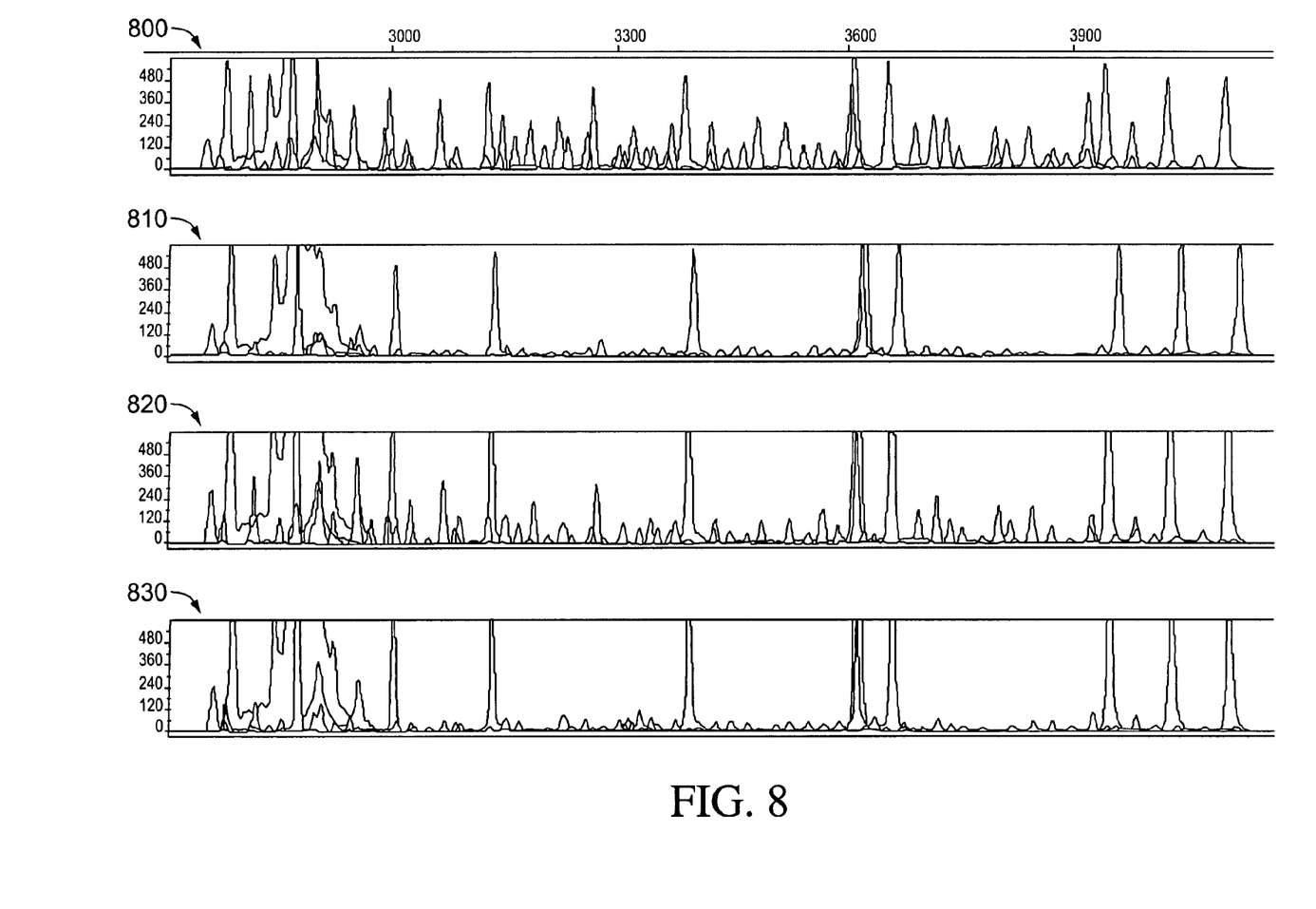
Figure 9:
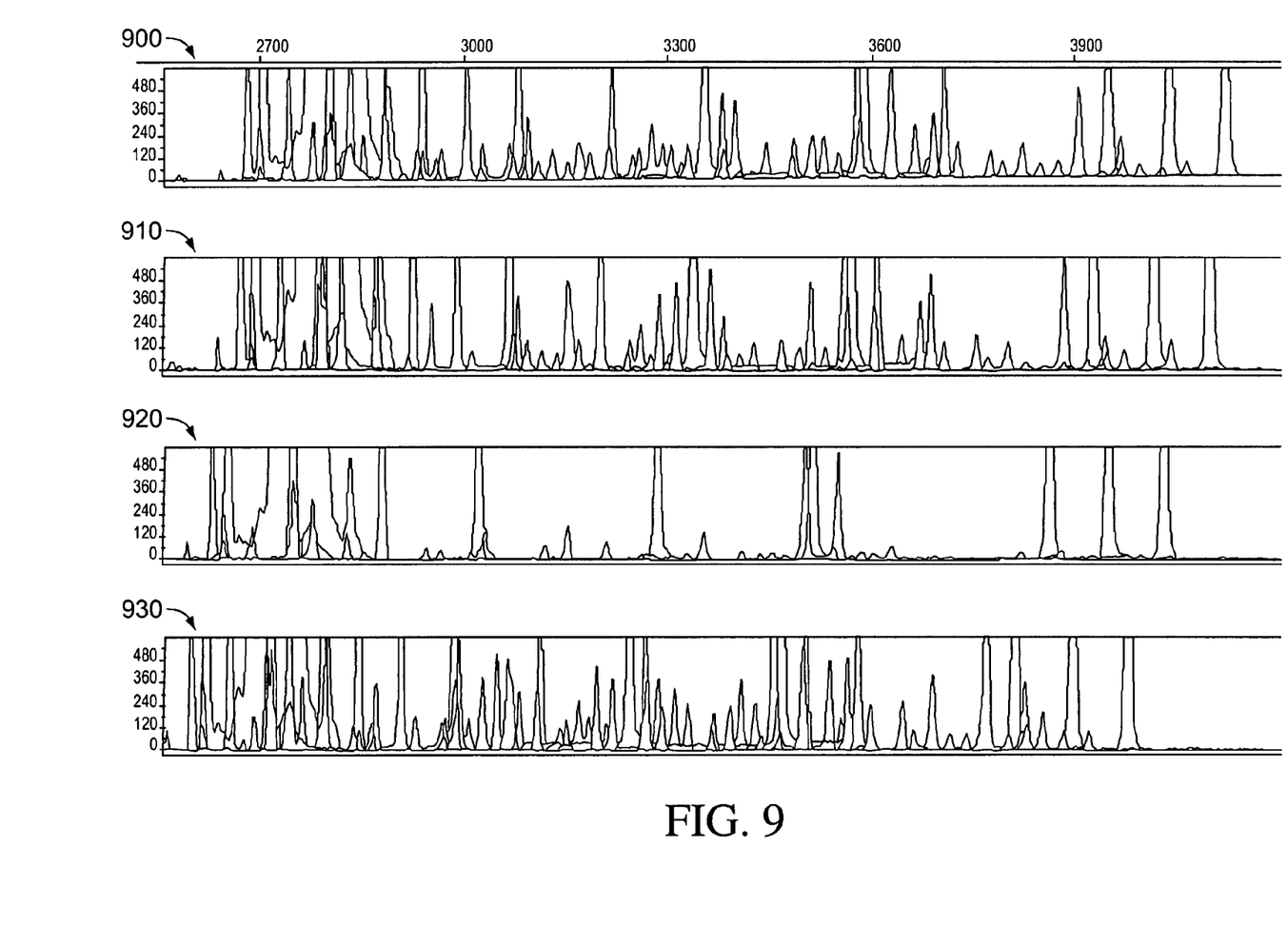

The SNP assay was implemented by showing each step in the process performed could be incrementally adopted to platforms. FIG. 7 illustrates the results from a control using manual transfers and analysis by capillary electrophoresis using ABI Prism® 310 Genetic Analyzer (Applied Biosystems, Foster City). Plot 700 illustrates the gDNA sequence that resulted from the SNP assay performed with manual transfers and plot 710 illustrates the non-template control for the same SNP assay performed with manual transfers. FIG. 8 illustrates the results when the OLA was conducted on an OLA platform (plots 800 and 820 illustrate gDNA and plots 810 and 830 illustrate non-template control) and FIG. 9 illustrates the results when the PCR was conducted on a PCR platform (plot 900 illustrates gDNA where OLA product was mixed with PCR master mix externally in 10 microliters; plot 910 illustrates gDNA where OLA product was mixed with PCR master mix directly in the PCR platform; plot 920 illustrate results from the non-template control; plot 930 illustrates gDNA where the OLA concentration was doubled when mixing with PCR master mix). The results show that OLA and PCR were conducted on platforms independently, that OLA products were dosed into the PCR master mix, and that OLA concentration does not substantially affect PCR performance.

Figure 10:
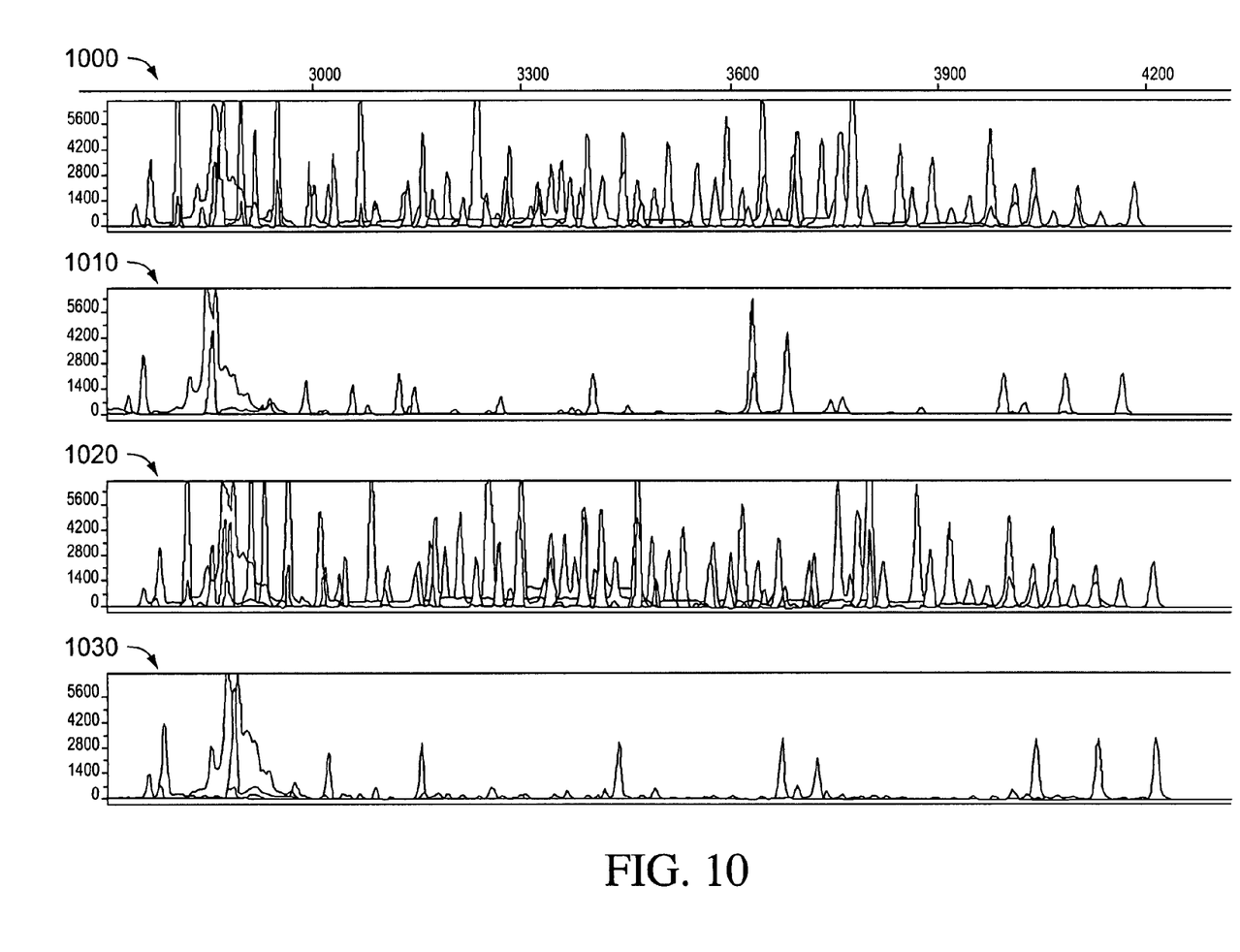
Figure 11:
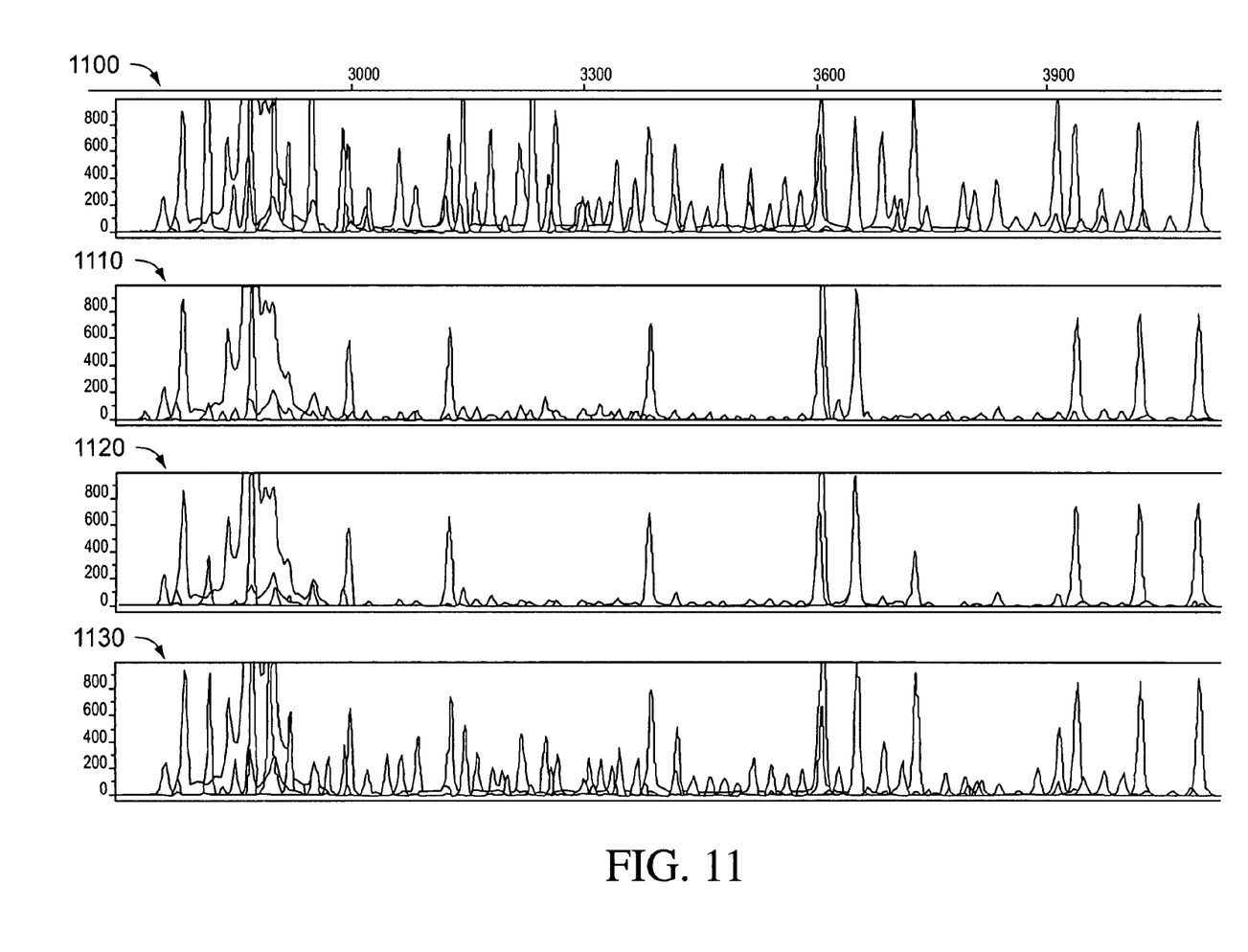
Figure 12:
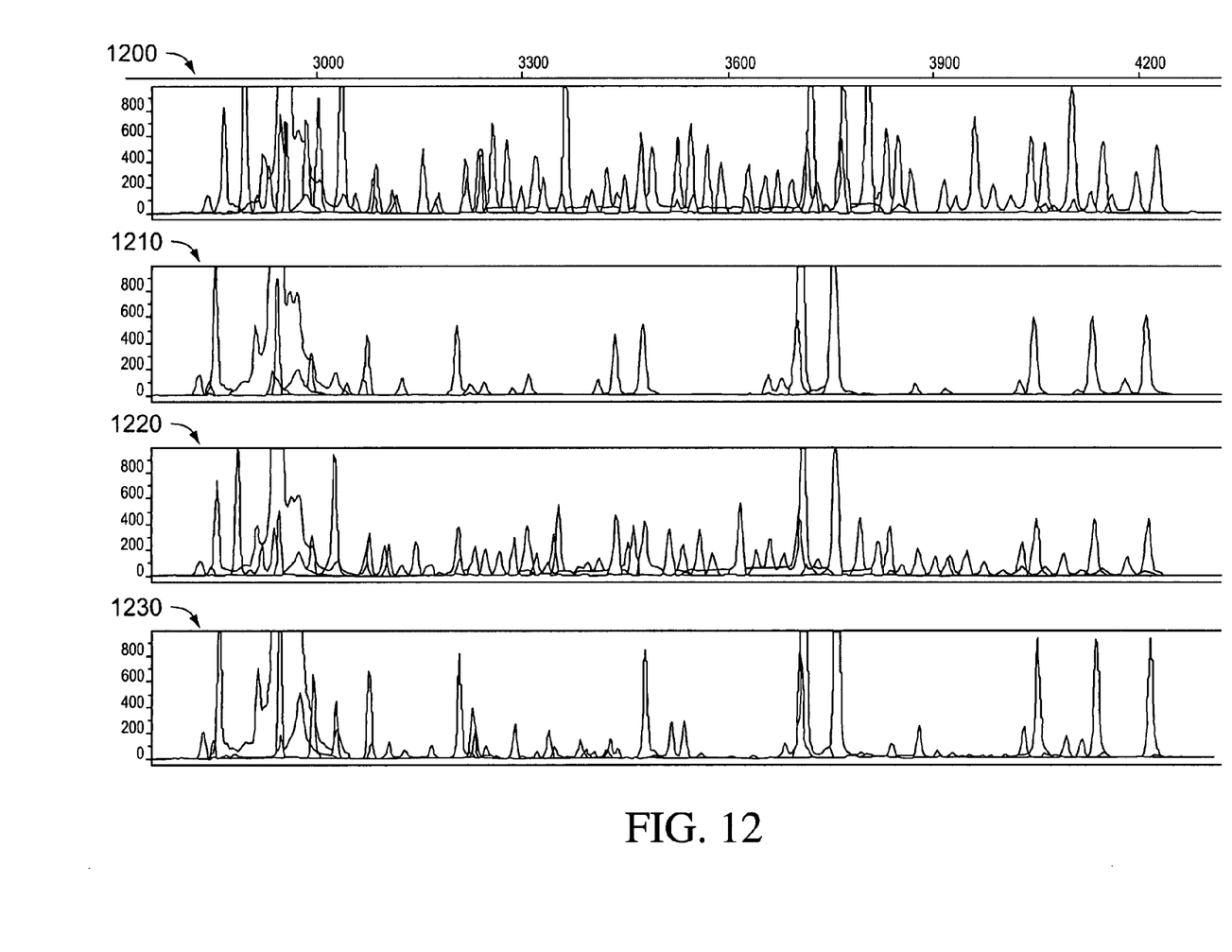
Figure 13:
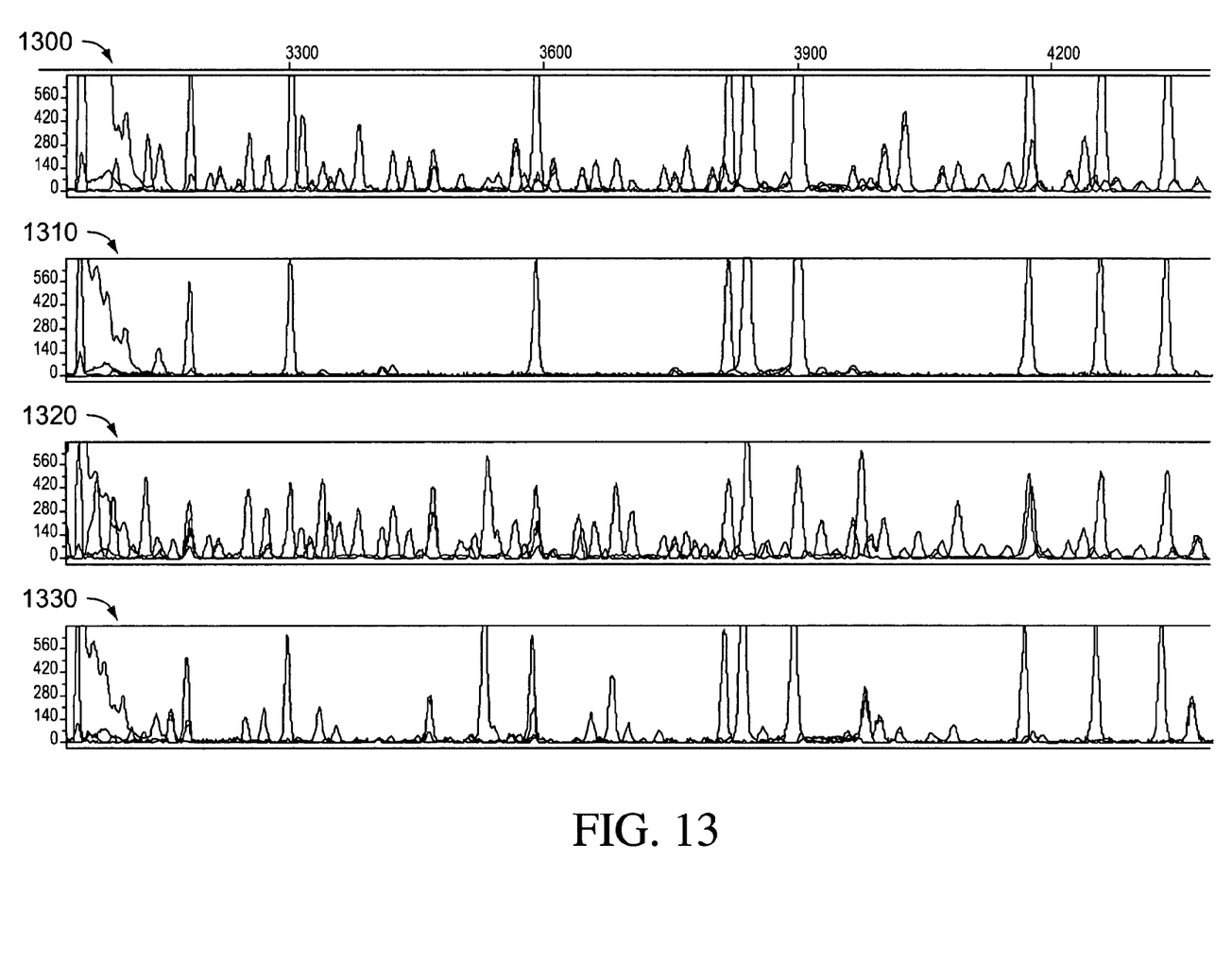
Figure 14:
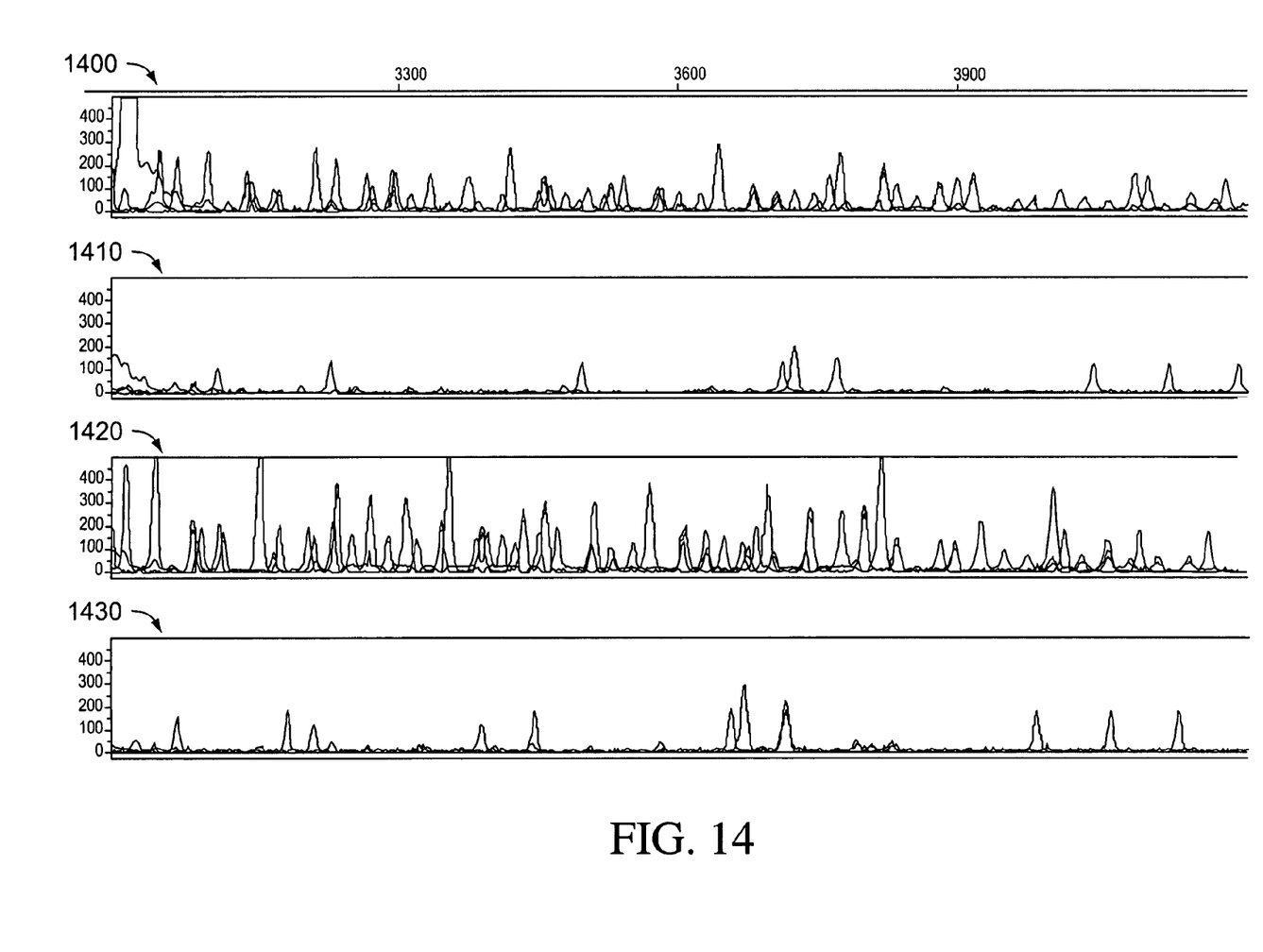

The SNP assay was implemented by showing that liquid transfers between each step in the process performed on a platform could be automated in a closed system. In the SNP assay, liquid transfers occurred between phosphorylation product and sample introduction, between master mix and OLA platform, between OLA platform and PCR platform and between PCR platform and microtiter plate. FIG. 10 illustrates the results from the assay steps up to transfer to microtiter plate performed on platforms or all assay steps performed in tubes as a non-platform control (plot 1000 illustrates gDNA on OLA platform and PCR platform; plot 1010 illustrates the non-template control; plot 1020 illustrates the non-platform control; plot 1030 illustrates the non-template control for the non-platform control). FIG. 11 illustrates the results from integrating the fluid transfer between the phorphorylation products and sample introduction (plot 1100 illustrates control gDNA; plot 1110 illustrates the non-template control; and plots 1120 and 1130 illustrate gDNA). FIG. 12 illustrates the results from integrating the fluid transfer between the OLA platform and the PCR platform (plot 1200 illustrates gDNA and plot 1210 illustrates the non-template control; plot 1220 illustrates gDNA and plot 1230 illustrates the non-template control). FIG. 13 illustrates the results from integrating drying down of OLA probes or gDNA. These materials were pre-filled in the wells of the platform and the remainder of the reactants were filled with capillary action through a fill-port. The rest of the assay steps were conducting as discussed above showing the dried-down reactants redissolve during thermal cycling (plot 1300 illustrates OLA probes and plot 1310 illustrates the non-template control; plot 1320 illustrates gDNA and plot 1330 illustrates the non-template control. FIG. 14 illustrates the results from the combined sequence of self-filling, OLA thermal cycling, and integrated pipetting for OLA purification without crosstalk between different well on the platform (plots 1400 and 1420 illustrate the samples and plots 1410 and 1430 illustrate the non-template control for each sample, respectively).

In various embodiments, steps can be integrated into one platform such as sample preparation, reaction and purification. Such integration can be facilitated by intra-platform microfluidic liquid transfers, for example, by capillary action. Example of systems that can perform such transfers include systems described in U.S. Pat. No. 6,776,965 and manufactured by processes described in U.S. Pat. No. 6,660,151. Supply of such systems can include platforms such as the Lilliput® chip manufactured by Boehringer Ingelheim microParts GmbH (Dortmund, Germany). In various embodiments, further step can be integrated into the closed system by adding platforms, as illustrated in chart 1, and performing inter-platform transfers as described above. Examples of such added platforms can include a post-PCR purification platform coated with streptavidin. Such platforms can include washing in the platform or an interface for washing.

In various embodiments, the OLA platform can be used to perform many different types of ligations, for example, proximity ligation. Proximity ligation can include padlock probes as described in U.S. Pat. Pub. No. 2005/0026204 A1 to perform assays including OLA and PCR as described in Gullberg, Mats, et al., *Cytokine detection by antibody-based proximity ligation,* PNAS, vol. 101, no. 22, pp. 8420-24 (2004). The proximity ligation mechanism can provide protein measurements by converting the detection of specific proteins to the analysis of DNA sequences. Padlock probes containing oligonucleotide extensions can bind in pairs to target proteins and form PCR amplifiable tag sequences by OLA ligation when brought into proximity. The padlock probe can include a polyclonal antibody or matched pairs of polyclonal antibodies with attached oligonucleotide sequences. The present teachings can provide a closed system for transferring the products of the OLA ligations in OLA wells on an OLA platform into PCR wells on a PCR platform for PCR amplification. The OLA wells can include the ligation of padlock probes and the PCR wells can include the amplification of the DNA sequences associated with the ligated oligonucleotides of the padlock probe. The present teachings provide reaction volumes and transfer volumes for performing the OLA and PCR of the proximity ligation mechanism in a closed system.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "less than 10" includes any and all subranges between (and including) the minimum value of zero and the maximum value of 10, that is, any and all subranges having a minimum value of equal to or greater than zero and a maximum value of equal to or less than 10, e.g., 1 to 5.

It is noted that, as used in this specification and the appended claims, the singular forms "a," "an," and "the," include plural referents unless expressly and unequivocally limited to one referent. Thus, for example, reference to "a charged species" includes two or more different charged species. As used herein, the term "include" and its grammatical variants are intended to be non-limiting, such that recitation of items in a list is not to the exclusion of other like items that can be substituted or added to the listed items.

It will be apparent to those skilled in the art that various modifications and variations can be made to various embodiments described herein without departing from the spirit or scope of the present teachings. Thus, it is intended that the various embodiments described herein cover other modifications and variations within the scope of the appended claims and their equivalents.

What is claimed is:

1. A system for detecting a target polynucleotide in a sample comprising:
   an oligonucleotide ligation assay (OLA) platform comprising a plurality of OLA wells; and
   a PCR platform comprising a plurality of PCR wells, wherein the OLA wells are in fluid communications with the PCR wells,
   wherein the OLA platform is in a first card and the PCR platform is in a second card, and wherein the first card and the second card are separate cards mated together, and
   wherein the system is a closed system capable of transferring a plurality of OLA products from the OLA wells to the PCR wells.

2. The system of claim 1, wherein the OLA wells comprise OLA probes.

3. The system of claim 1, wherein the PCR wells comprise PCR reagents.

4. The system of claim 1, wherein each OLA well is in fluid communication with a corresponding PCR well.

5. The system of claim 1, further comprising a purification platform.

6. The system of claim 5, wherein the purification platform comprises coated beads.

7. The system of claim 6, wherein the coated beads are magnetic.

8. The system of claim 6, wherein the coated beads comprise streptavidin.

9. The system of claim 1, wherein the OLA wells provide 1 microliter volumes, and wherein the PCR wells provide 1 microliter volumes.

10. The system of claim 9, further providing a transferring system on the OLA platform, wherein the transferring system is sized for at least 70 nanoliters of OLA product from each OLA well to reach a corresponding PCR well.

11. A method for detecting a target polynucleotide in a sample comprising:
   providing an oligonucleotide ligation assay (OLA) platform comprising a plurality of OLA wells;

providing a PCR platform comprising a plurality of PCR wells, wherein the OLA wells are capable of fluid communications with the PCR wells;

providing the sample to the OLA platform;

thermal cycling the sample in the OLA wells;

mating the OLA platform to the PCR platform to provide fluid communication between each of the OLA wells and each of the PCR wells;

transferring a plurality of OLA products to the PCR platform;

thermal cycling the OLA products in the PCR wells; and detecting the target polynucleotide in the sample.

12. The method of claim 11, further comprising purifying a plurality of PCR products after thermal cycling the OLA products in the PCR wells.

13. The method of claim 11, wherein providing the OLA platform comprises positioning OLA probes in the OLA wells.

14. The method of claim 11, wherein providing the PCR platform comprises positioning PCP reagents in the PCP wells.

15. A system for detecting a target polynucleotide in a sample comprising:

a first platform comprising a first plurality of wells configured to a first bioassay; and a second platform comprising a second plurality of wells configured to a second bioassay, wherein the first plurality of wells are in fluid communications with the second plurality of wells, wherein the first platform is in a first card and the second platform is in a second card, and wherein the first card and the second card are separate cards mated together, wherein the system is a closed system capable of transferring a plurality of products from the first plurality of wells to the second plurality of wells, wherein the system does not comprise a purification material between the first plurality of wells and the second plurality of wells, and wherein the fluid communication comprises a microfluidic transfer from the first platform to the second platform.

16. The apparatus of claim 15, further comprising a plurality of purification chambers between the second plurality of wells and an outlet, wherein the purification chambers are in fluid communication with the second plurality of wells.

17. The apparatus of claim 16, wherein the plurality of purification chambers comprised coated beads.

18. The apparatus of claim 17, wherein the coated beads are magnetic.

19. The apparatus of claim 15, wherein the first bioassay is oligonucleotide ligation assay (OLA) and the second bioassay is PCR.

20. The apparatus of claim 15, wherein the first bioassay is gDNA preparation and the second bioassay is OLA.

21. The apparatus of claim 20, further comprising a third platform comprising a third plurality of wells configured to a third bioassay, wherein the second plurality of wells are in fluid communications with the third plurality of wells such that each well in the third plurality corresponds to a well in the second plurality, wherein the third bioassay is PCR.

* * * * *